United States Patent [19]

Kwan-Gett

[11] Patent Number: 4,976,730
[45] Date of Patent: Dec. 11, 1990

[54] ARTIFICIAL PERICARDIUM

[76] Inventor: Clifford S. Kwan-Gett, 3017 St. Mary's Circle, Salt Lake City, Utah 34108

[21] Appl. No.: 258,180

[22] Filed: Oct. 11, 1988

[51] Int. Cl.⁵ .............................................. A61M 1/10
[52] U.S. Cl. ..................................................... 623/3
[58] Field of Search .................. 623/3, 22, 1; 600/16, 600/17; 128/64

[56] References Cited

U.S. PATENT DOCUMENTS

| | | | |
|---|---|---|---|
| 3,771,173 | 11/1973 | Lamb, Jr. | 623/3 |
| 4,355,426 | 10/1982 | MacGregor | 623/3 |
| 4,442,133 | 4/1984 | Greco et al. | 623/1 |
| 4,573,997 | 3/1986 | Wisman et al. | 623/3 |
| 4,583,525 | 4/1986 | Suzuki et al. | 600/16 |
| 4,781,715 | 11/1988 | Wurzel | 623/3 |
| 4,795,469 | 1/1989 | Oh | 623/22 |
| 4,795,470 | 1/1989 | Goymann et al. | 623/22 |

FOREIGN PATENT DOCUMENTS 0247015 11/1987 European Pat. Off. ............. 600/16

Primary Examiner—Randall L. Green
Assistant Examiner—Stephanie L. Iantorno
Attorney, Agent, or Firm—Trask, Britt & Rossa

[57] ABSTRACT

An artificial pericardium is a sac formed with an opening into which an artificial blood pumping device is positioned. Apertures with collars are secured to blood inlets and outlets as well as operation signal lines. The sac is closed and a fluid is injected into the sac to urge the sac outwardly against the surrounding tissue.

22 Claims, 2 Drawing Sheets

ARTIFICIAL PERICARDIUM

BACKGROUND OF THE INVENTION

1. Field:

This invention relates to artificial organs, and more particularly to artificial blood pumping devices including artificial hearts. More specifically, this invention relates to an artificial pericardium within which an artificial blood pumping device is positioned.

2. State of the Art:

In late 1982, an artificial heart was implanted in Dr. Barney Clark, bringing to national attention artificial organs in general and the utility of an implantable total artificial heart. The artificial heart implanted in Dr. Barney Clark is generally illustrated and described in *Newsweek*, "An Incredible Affair of the Heart," Dec. 13, 1982, pages 70–74, 79. In addition to the artificial heart, there are also other implantable artificial blood pumping devices known to those skilled in the art including an artificial ventricle or right heart assist device to assist the heart or to even replace one of the two ventricles in given circumstances.

Presently, artificial hearts are powered by air supplied by a driver via tubes which penetrate through the chest wall for connection to the artificial heart or the artificial ventricle. Electrically powered hearts are presently being considered but are not yet known to be in clinical use. *Scientific American*, January 1981, vol. 244, no. 1, pages 74–80.

Presently, a right heart assist device or artificial ventricle and an artificial heart are simply positioned within the chest of the patient and connected for operation. The body naturally has formed a pericardial membrane about the heart which membrane is surgically opened in order to provide access to the patient's natural heart and to facilitate placement of an artificial blood pumping device adjacent to or in the location of the natural heart, should the natural heart be removed. The natural pericardium is not thereafter closed, typically because it is not large enough. The surface of the artificial blood pumping device is thus exposed to the various body fluids and organs in the immediate vicinity. The substantial surface area of the artificial blood pumping device also provides an increased surface area for chemical interaction with the body, and in turn may exacerbate the potential for foreign body rejection. The surface area over which infection and other undesirable bacteriological developments may occur after the placement of the artificial blood pumping device is also increased. Also, one or more small voids, abscesses, spaces or pockets may be formed by the artificial blood pumping device and the body tissue in which bacteria may be deposited and thereafter grow into an infection.

At present, there is no structure or procedure available to minimize the surface area of the artificial blood pumping device exposed to living tissue to reduce infection and to otherwise enhance the survivability of the artificial blood pumping device within the body cavity.

SUMMARY OF THE INVENTION

An artificial pericardium is provided for use in a patient in conjunction with an artificial blood pumping device having at least one blood inlet line and one blood outlet line. The artificial pericardium comprises a sac formed of a flexible material suitable for placement within the body of a patient. The sac is sized to snugly receive the artificial blood pumping device. The sac has an opening sized to pass the artificial blood pumping device therethrough. The opening is operable between an open condition, for passing the artificial blood pumping device therethrough, and a closed condition, in which fluid flow through the opening is inhibited. The sac also contains apertures sized and positioned to substantially register with, and to have pass through, the blood inlet and outlet lines when the artificial blood pumping device is positioned within the sac. The sac also includes connector means adapted at each of the apertures for connecting the blood inlet line and the blood outlet line thereto.

Upon placement of the artificial blood pumping device within the artificial pericardium and operating the opening to its closed condition, fluid may be added in sufficient quantity to fill the volume between the external surface of the artificial blood pumping device and the sac. The fluid is preferably a liquid and a combination of a base and a drug selected from the classes of drugs used to treat and resist infections. The sac is formed to be slightly elastic and fluid resistant. That is, fluids cannot readily pass therethrough. Most desirably, the fluid is inserted at a pressure to urge the sac outwardly and snugly against the surrounding tissue.

Desirably the sac is shaped to conform to the major contours of the artificial blood pumping device and simultaneously to approximate the contour of the tissue or cavity into which the artificial pericardium with artificial blood pumping device is to be placed. Also, it is desirable that the exterior surface of the sac be impregnated or coated with an infection resistant substance.

Alternately, the sac may be formed of a compliant material in which deformation due to inward pressure in one area produces rapid deformation of the entire surface of the sac remote from the area in which the inward deformation is occurring. In yet other alternatives, the sac may be formed of any one of the classes of materials chemically acceptable for placement within the body, including polyurethane, silicone rubber, TEFLON (polytetrafluoroethylene) and nylon.

In preferred embodiments, the connector means of each aperture is an elastic tube sized to snugly surround its respective line. Most desirably, the connector means includes securing means for placement about the elastic tube to secure the elastic tube to its respective line.

The closing means is associated with the opening and is operated as above noted. One desirable closure means is a zipper. Another alternative closure means is a grooved seal having male and female portions sized for effecting a sealing closure.

In yet another embodiment, the artificial pericardium of the instant invention includes an injection site formed in the sac to receive needles therethrough and to seal upon removal. The injection site is used for extracting from and injecting fluids into the sac. The artificial pericardium also may include a pressure sensing means positioned within the sac to sense the pressure of fluids therein. The pressure sensing means may have means to communicate signals reflective of the sensed pressure exterior of the sac and via signal communication means to external the body of the patient.

In a preferred embodiment, the sac is formed into sections which may be regarded as an upper and lower section. The upper section is formed with apertures and connection means to interconnect to drive lines for driving the artificial blood pumping device positioned within the sac. The lower half is provided with multiple apertures, and preferably four apertures, to correspond with the venous, arterial and pulmonary vessels of a natural heart. Securing means are associated with the apertures for securing the artificial pericardium thereto. The upper and lower sections may be rotated relative to each other when sealably joined together to form the sac.

BRIEF DESCRIPTION OF THE DRAWINGS

In the drawings which illustrate the best mode presently contemplated for carrying out the invention.

DETAILED DESCRIPTION OF THE PREFERRED EMBODIMENTS

Figure 1:
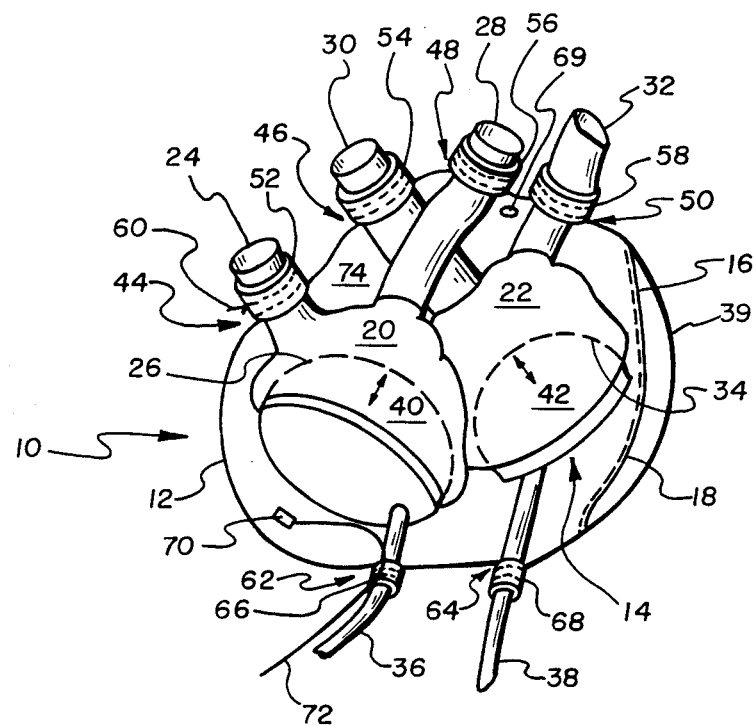
FIG. 1 is a perspective depiction of a transparent artificial pericardium of the instant invention with an artificial heart positioned therewithin.

Referring to FIG. 1, an artificial pericardium of the instant invention is generally depicted by the number 10. It includes a sac 12 here shown with an artificial blood pumping device which in fact is a total artificial heart (TAH) generally identified by the number 14.

An opening 16 is formed in the sac and is sized for passing the artificial blood pumping device such as the TAH 14 therethrough. Closure means 18, which is more clearly described hereinafter, is mechanically associated with the opening 16 for operating the opening 16 between an open condition and a closed condition. In the open condition, the artificial blood pumping device may pass therethrough. In the closed condition, fluid flow through the opening 16 is inhibited and desirably prohibited. That is, a substantially fluid-tight seal or closure is effected.

The artificial blood pumping device must have at least one blood inlet line and one blood outlet line. In FIG. 1, the artificial blood pumping device is shown to be the TAH 14 which has a right ventricle 20 and a left ventricle 22. Blood is received by the right ventricle 20 from the right atrium via an inlet 24. A pumping membrane 26 urges the blood outward via outlet 28 to the pulmonary system. The blood returns from the pulmonary system via inlet 30 for further pumping by the left ventricle 22 and discharge via the outlet 32 to the arterial system of the patient.

As shown in FIG. 1, the left ventricle 22 and right ventricle 20 each have flexible membranes 26 and 34 which are operated by air pressure supplied via signal lines 36 and 38. That is, air is supplied to the cavity 40 and cavity 42 to cause the diaphragms 26 and 34 to flex and in turn cause blood to be pumped. Upon exhausting of air via lines 36 and 38, the diaphragms 26 and 34 are collapsed by blood pressure to allow the respective ventricles 20 and 22 to fill.

It should be understood that alternate blood pumping devices may be employed within the artificial pericardium of the instant invention. Electrical pumps powered by an internal power source (i.e., battery) or an external power source via power lines are within contemplation. That is, the signal lines 36 and 38 may supply electrical signals in lieu of or in addition to air signals.

In FIG. 1, it can be seen that apertures are formed in the sac surface 39 to substantially register with and have pass therethrough the blood inlet and outlet lines. More specifically, in the embodiment illustrated in FIG. 1, apertures 44, 46, 48 and 50 are formed in the sac surface 39 to register with the blood inlet and outlet lines 24, 30, 28 and 32 as above described. Connector means 52, 54, 56 and 58 are adapted to the sac 12 at each of the apertures 44, 46, 48 and 50, respectively, for connecting the blood inlet and blood outlet lines thereto. As here shown, the connector means includes sleeves or collars which may either be sealingly stitched to or unitarily formed with the sac 12 through which the inlet lines and outlet lines 24, 30, 28 and 32 pass. The connector means 52 is shown to have securing means 60 which is here comprised of a suture which is stitched around the collar 52 and snugly secured to the line 24. A plurality of sutures or ligatures may be used to effect a substantially fluid-tight seal. Similar suturing arrangements are desirably used for each of the other collars 54, 56 and 58. Other securing means may be used, including clamps, elastics or rubber bands, or any other similar device intended to sealably secure a sleeve or collar to an inlet line.

It should be clearly understood that the inlet lines 24 and 30 and outlet lines 28 nd 32 are also sealably secured to the artificial blood pumping device such as the TAH 14 in FIG. 1 by means such as sutures or clamps as typically associated with the medical procedures adopted for emplacing such devices. Desirably the connection is effected to be interior the sac 12.

It should also be noted that the pumping signal supply lines 36 and 38 also are interconnected through the sac 12 via apertures 62 and 64 which have connector means associated therewith which are sleeves or collars 66 and 68. The sleeves or collars 66 and 68 are each sealingly secured to the lines 36 and 38 by securing means such as sutures similar to the sutures 60.

It may be noted that FIG. 1 shows the sac 12 to be fabricated of a transparent material so that the interior artificial blood pumping device can be clearly seen. In reality, it may or may not be transparent but is here shown to be such simply for purposes of clarity and illustration. In practice, the sac 12 is formed of any class or category of material suitable for placement within the body, and one which is chemically acceptable therewith, including polyurethanes, silicone rubbers, TEFLON (polytetrafluoroethylene) and nylons. In some circumstances, it may be desirable to select a material from the above categories or classes structured in the form of a mesh in which tissue becomes associated therewith and forms a relatively germ-free inner surface. That is, the surrounding tissue may closely adjoin to and microscopically interweave into the surface structure of the sac. Alternately, a silicone rubber type material may be used which provides for a slippery nonadhering interface with surrounding tissue. In most cases, however, the surface of the sac 12 is desirably impregnated with any one of a number of different drugs to provide desired therapeutic benefits. In particular, it may be impregnated with various types of infection-resisting drugs, specifically antibiotics.

In FIG. 1, the sac 12 may also include one or more injection sites 69. The injection site 69 is formed of the type of material through which a hollow needle may be inserted and later removed without leaving a puncture or opening. That is, the material has an elasticity associated with it which results in a resealing upon removal of the needle. Such material may be that which is presently used, for example, for injection sites in intravenous systems and intravenous catheters.

The sac 12 also has an interior pressure sensor positioned on the interior surface to sense the pressure within the sac 12 when the opening 16 has been closed by operation of the closure means 18. The pressure sensor has means to communicate a signal reflective of the pressure external the sac 12 and external the patient. In FIG. 1, the interior pressure sensor is shown to be a pressure transducer 70 which communicates an electrical signal reflective of the pressure sensed via a conductor 72 which is here shown to be closely associated with the operation signal line 36 to pass through the aperture 62 and collar 66 of the communication line 36, or alternately the other communication line 38. Indeed, it may pass through any available closely proximate aperture formed in the sac 12.

To use the artificial pericardium of the instant invention, a patient is typically prepared for surgery and undergoes surgery to effect the removal of the patient's natural heart. Of course, the patient is interconnected to an artificial heart/lung machine and is in turn being maintained thereon as part of the overall life support effort during the involved surgery.

Upon removal of the natural heart, the sac 12 is positioned appropriately within the available cavity within the body of the patient. The various body vessels which act as the inlets and outlets 24, 30, 28 and 32 are passed through the appropriate collars 52, 54, 56 and 58. Thereafter, the artificial blood pumping device such as the TAH 14 is passed through the opening 16 which has been opened by operation of the closure means 18 to its open condition. Thereafter, the artificial blood pumping device is interconnected to the body vessels such as vessels 24, 30, 28 and 32, as known to those skilled in the art. The collars 52, 54, 56 and 58 are secured by appropriate ligature, suture, clamps or other acceptable means about its respective vessel 24, 30, 28 and 32. Similarly, the operation lines 36 and 38 are passed through their respective collars and openings 62, 64, 66 and 68 for interconnection to the right 20 and left 22 ventricles of the artificial heart 14 illustrated in FIG. 1. Similarly, the pressure sensing line 72 is passed through the closest available opening or another opening as desired to pass exterior the body with the air supply lines 36 and 38. Indeed, air supply lines 36 and 38 may include an embedded conductor in their respective sidewalls to avoid use of a separate connector passing through the chest wall of the patient under treatment.

Upon securing the collars 66 and 68 to their respective lines 36 and 38, the closure means 18 may be operated to its closed position. Thereafter, a needle or syringe may be inserted through the injection site 68 to extract undesired fluid such as air from the interior 74 of the sac 12. Thereafter, desired fluid, which could, for example, be a simple salt solution, can be inserted through the injection site 68 to interior 74 of the sac 12 to totally surround the artificial blood pumping device positioned therewithin. Indeed, the fluid inserted is preferably a base coupled with any acceptable therapeutic drug which may resist infection including, for example, available and desired antibiotics. Thereafter, the artificial blood pumping device such as the artificial heart 14 may be energized and activated and in turn used to replace the artificial heart/lung machine being used as a life support mechanism during the course of the above-described surgical procedures.

The pressure transducer 70 is connected to an external indicator 109 (FIG. 2) so that the pressure internal of the sac 12 may be detected and observed. By such means, the pressure within the sac 12 may be monitored, in turn controlling the amount of fluid being injected via site 68. Leakage in or out can also be monitored. Upon activation of the artificial blood pumping device such as the artificial heart 14, further closure may be effected, including eventual closure of the chest wall of the patient. Thereafter, the pressure transducer 70 continues to relay signals reflective of the pressure within the sac to in turn reflect any abnormal pressure being exerted on the sac 12 either from exterior the sac 12 or as a result of leakage within the sac 12 from a connection to the artificial blood pumping device. It may also sense air pressure in the event there is leakage of air.

Notably, the fluid inserted into the interior of the sac 12 is at a pressure to urge the surface 39 of the sac 12 outwardly against the surrounding tissue. A pressure is selected to effect a snug interface to preclude the formation of pockets, recesses or abscesses. Various bacteria in the pockets, recesses or abscesses could grow and create an infection. However, a snug interface allows for blood to be present to preclude the development of such an infection. The elastic character of the sac 12 allows the surface 39 to distort and conform to the surrounding tissue to preclude formation of the pockets, recesses or abscesses and in turn reduce the risk of infection and in turn the need to administer large quantities of medication to treat any infections that may thereafter arise.

Indeed it may be noted that the total surface area of the artificial pericardium 10 is substantially smaller or less than the outer surface area of the artificial blood pumping device positioned therewithin. Thereby the total surface area for the growth of infectious organisms is substantially reduced, enhancing the viability of the surgical procedures and improving the probability of a successful implantation. Indeed, the probability of infection and the need for use of anti-infection medication are reduced because more chemically acceptable materials are positioned to interface with the tissue or flesh of the involved patient.

Figure 2:
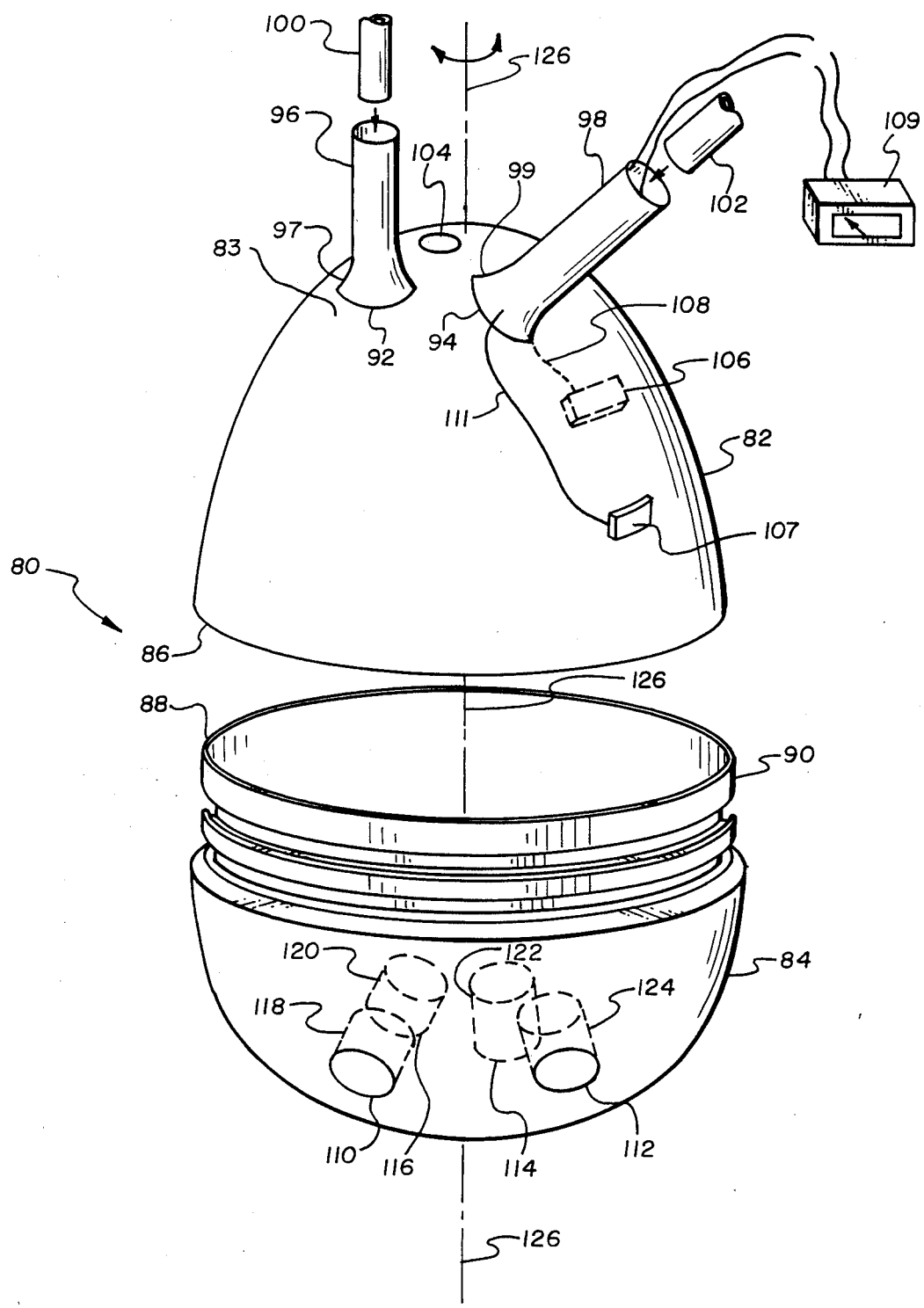
FIG. 2 is a perspective depiction of an alternate embodiment of the instant invention.

Referring now to FIG. 2, an alternate artificial pericardium is shown to be comprised of a sac 80 having an upper section 82 and a lower section 84. The upper 82 and lower 84 sections are each shown to be substantially hemispherical for purposes of convenience in illustration. Both may be of any acceptable shape or configuration desired by the user so long as they may be joined to form the entire sac 80, as more particularly described herein. Applicant presently believes that this substantial hemispheric construction such as that shown in FIG. 2 for the sections 82 and 84 will be preferable.

As stated, the upper section 82 is to be joined to the lower section 84 to form the sac 80. The opening is thus defined by the entire perimeter 86 and 88 of the upper 82 and lower 84 sections, respectively. Associated with the opening defined by the perimeters 86 and 88 are closure means which are desirably a male/female co-acting snap arrangement, which is more fully described and discussed hereinafter but which is shown in part 90 in FIG. 2. That is, the closure arrangement in the lower section 84 can be seen. The closure arrangement in upper section 82 is interior and in turn not shown.

As here shown, the upper section 82 has apertures 92 and 94 with collars 96 and 98, respectively, for interconnection of operation signal means 100 and 102 similar to tubes 36 and 38 illustrated in FIG. 1. The collars 96 and 98 are unitarily formed as part of the upper section 82. It should be noted that collars 96 and 98 may be made of a diameter or cross section smaller than that of tubes 100 and 102. The collars 96 and 98 are then fabricated from an elastic-type material such that when the tubes 100 and 102 are passed therethrough, they elastically deform to snugly surround the tubes 100 and 102 to facilitate effecting a seal between the collars 96, 98 and their respective tubes 100 and 102. The collars 96 and 98 are formed to have an arcuate surface 97 and 99 between the surface 83 of the upper half 82 and the collar itself 96 and 98 generally as shown. The arcuate surfaces 97 and 99 reduce the creation of corners and recesses or abscesses and in turn reduce the risk of infection.

The upper section 82 is also shown to include an injection site 104 and an internal pressure sensing transducer 106 which is interconnected via conductor 108 to extend exterior the sac 80 and in turn exterior the patient for connection to a pressure indicating device 109 for viewing external the patient. An optional pressure sensing transducer 107 is shown to sense the pressure external the sac 12 in the body after closure of the chest cavity. The transducer 107 supplies pressure reflective signals via conductor 111 to the external indicating device 109.

The lower section 84 is here shown to have a plurality of apertures 110, 112, 114 and 116 to receive and supply blood. Each aperture has associated therewith a collar 118, 120, 122, and 124, which are here shown in phantom to extend interior the sac 80. Thus, the connector means are in effect positioned interior the sac 80 in FIG. 2 as opposed to exterior the sac as shown with respect to FIG. 1. Applicant presently believes it is desirable to have the connector means such as collars 118, 120, 122 and 124 extending interior the sac 80 to minimize the surface available for the growth of infectious organisms exterior the sac in the body of the patient. The collars are joined to the sac by acceptable means or unitarily formed as part of the sac 80.

In use, it is presently envisioned that an artificial blood pumping device, such as an artificial heart similar to heart 14 of FIG. 1, may be inserted into the lower section 84 of the sac 80 so that various connections can be effected not only to the inlet and outlet for blood, but also to effect a sealing relationship between those inlets and the lower section 84 of the sac 80. Thereafter, connection can be effected to the external driver for operation via supply lines 100 and 102 via collars 96 and 98, which are here shown external the sac but which may also be internal the sac. Indeed, the collars 96 and 98, as well as collars 118, 120, 122 and 124, may be positioned in either direction by simply folding them or inserting them inward or outward similar to a stocking or a coat sleeve. Thereafter, the upper section 82 can be joined to the lower section 84 by operating the closure means to place the opening in a closed condition so that fluid flow therethrough is inhibited. Thereafter, any trapped gases or fluids that are undesired may be extracted through the injection site 104 and desired fluids inserted as hereinbefore described with respect to FIG. 1. It may be particularly noted that upper section 82 may be rotated around axis 126 to provide desired alignment of the various apertures 92, 94, 110, 112, 114, and 116 to accommodate the artificial blood pumping device positioned within the sac 80 as well as to accommodate to the form, shape, and dimensions of the body cavity into which the artificial pericardium is being positioned.

Figure 3:
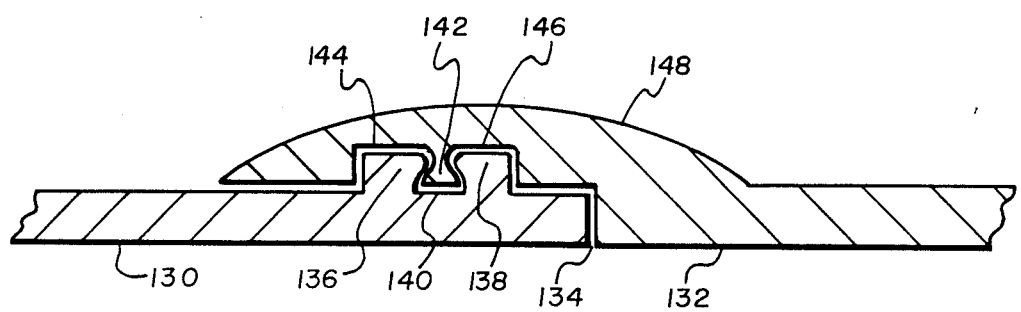
FIG. 3 is a partial cross-section view of a closure means for use with the instant invention.

Referring now to FIG. 3, a substantially enlarged partial cross-section of closure means for closing the opening in the sac 80 is illustrated. In particular, it shows a first section 130 and a second section 132 with a co-acting closure means unitarily formed therein. The closure means and the sections 130 and 132 are shown substantially enlarged for purposes of illustration. Further, they are shown somewhat spaced apart with a gap 134 for clarity. Desirably, the section 130 would snugly abut the section 132 to minimize the potential sites for infectious organisms along the juncture of the sections 130 and 132.

As here shown, the first section 130 is formed to have a pair of upstanding posts 136 and 138 as shown which in turn define a cavity 140 into which a corresponding post 142 formed in the second section 132 is snugly received. Notably, the posts 136 and 138 fit snugly into corresponding openings 144 and 146 formed in the second section 132. The posts 136, 138 and 140 have narrow bases and enlarged heads as shown.

The second section 132 is formed with an increased thickness area 148 to accommodate the forming of various components of the closure means as hereinbefore described. The closure means here illustrated in FIG. 3 is similar to that used in today's commercially available ZIP-LOCK ® bags. Other closure means may be conventional plastic zippers involving a plastic trolley with a plastic pullstrip. Other acceptable closures may no doubt be devised so long as they substantially preclude the transfer of fluids into and out of the sac. It is presently contemplated that the seal be liquid-tight. However, some benefit may be obtained even if a liquid-tight seal is not obtained. By liquid-tight, a conventional meaning is intended in which the migration of a substantial volume of fluid is precluded. Some microscopic migration may be possible or indeed present, depending on the type of seal selected.

It should be noted that the injection of fluid into the sac 12, 80 may be effected by use of a large syringe. Similarly, the air in the sac 12 and 80 may be extracted by use of a syringe. The fluid inserted is at a pressure to cause the sac 12, 80 to expand and conform to the surrounding tissue to prevent the formation of cavities or abscesses next to living issue. Thus, infections which can evolve at such locations are effectively avoided.

Most notably, the many corners and cavities of the artificial blood pumping device are from tissue contact eliminated, and thus the potential for infection and even rejection is reduced. In effect, there is no living tissue inside the artificial pericardium, which is smoothly interfaced to the surrounding tissue by the conforming surface of the sac 12, 80. Indeed, the material of construction is selected to be highly flexible and elastic to facilitate conformation to the surface of the body cavity into which it is placed.

It is to be understood that the embodiments of the invention and methods disclosed above are merely illustrative of the application of the principles of the inventions. Reference herein to details and steps or apparatus is not intended to limit the scope of the claims which themselves recite those features regarded as essential to the invention.

I claim:

1. An artificial pericardium comprising:
   a sac for positioning in the body of a patient to receive an artificial blood pumping device, said sac being formed of a substantially liquid impermeable material suitable for use int he body, said sac being deformable to conform to the shape of the cavity in the body into which it is to be placed, said sac being formed into an upper section and a lower section, sealably joinable by closure means unitarily formed therein, said upper section and said lower section being rotatable with respect to each other after joinder by said closure means;

first aperture means formed in said upper section to receive pumping signal supply lines operating from external said sac and external said patient to said blood pumping device; and second aperture means formed in said lower section to register with a blood inlet line from the body and to register with a blood outlet line to the body.

2. The artificial pericardium of claim 1 wherein said second aperture means includes:

vessel apertures to receive blood from the patient's venous system, to supply blood to the patient's pulmonary system, to receive blood from the patient's pulmonary system and to supply blood to the patient's arterial system.

3. The artificial pericardium of claim 2 wherein said aperture means includes connection means for sealably connecting to each signal supply line and at each of said vessel apertures for sealably connecting to blood vessels.

4. The artificial pericardium of claim 3 further including a fluid positionable within said sac with said first section and second section joined and with each connection means sealably connected to its respective line and vessel, said fluid being at a pressure to urge said sac outwardly and snugly against the surrounding tissue.

5. The artificial pericardium of claim 4 further including an injection site for inserting and extracting said fluid.

6. The artificial pericardium of claim 4 wherein said sac surface is impregnated with a desired drug and wherein said fluid includes a selected drug.

7. An artificial pericardium for use in a patient with an artificial blood pumping device comprising at least one blood pumping chamber and an exterior housing, said housing defining an external surface of said blood pumping device, and said artificial blood pumping device having at least one blood inlet line and one blood outlet line, said artificial pericardium comprising:

a sac formed of flexible material suitable for placement within the body of a patient, said sac being sized to snugly receive therewithin said artificial blood pumping device;

an opening formed in said sac sized for passing said artificial blood pumping device therethrough and operable between an open condition for passing said artificial blood pumping device therethrough and a closed condition in which fluid flow through said opening is inhibited;

closure means mechanically associated with said opening for operating said opening between an open condition and said closed condition;

apertures formed in said sac to substantially register with and have pass through said blood inlet and outlet lines when said artificial pumping device is positioned within said sac; and connector means adapted to said sac at each of said apertures for substantially sealingly connecting said blood inlet and blood outlet lines thereto to inhibit fluid flow between said sac and exterior said sac past said blood inlet and outlet lines.

8. The artificial pericardium of claim 7 further including a fluid placed within said sac with said artificial blood pumping device positioned within said sac, said fluid being of sufficient quantity to fill the volume between the external surface of the artificial blood pumping device and said sac.

9. The artificial pericardium of claim 8 wherein said fluid is a combination of a base and a drug selected from the class of drugs used to treat and resist infections.

10. The artificial pericardium of claim 8 wherein said sac is formed of a slightly elastic and fluid resistant material and wherein said fluid within said sac is at a pressure to urge the sac outwardly and snugly against the surrounding tissue.

11. The artificial pericardium of claim 7 wherein said sac is formed of a slightly elastic and fluid resistant material.

12. The artificial pericardium of claim 11 wherein said sac is shaped to conform to the major outer contours of the artificial blood pumping device and simultaneously to approximately the contour of the tissue defining the cavity into which the artificial pericardium with artificial blood pumping device is to be placed.

13. The artificial pericardium of claim 12 wherein said sac is formed of a material impregnated or coated with an infection resistance substance.

14. The artificial pericardium of claim 12 wherein said sac is formed of a compliant material in which deformation due to inward pressure in one area produces a rapid deformation of the entire surface of the sac.

15. The artificial pericardium of claim 12 wherein said sac is formed from any one of the classes of materials including polyurethane, silicone rubber, polytetrafluoroethylene and nylon.

16. The artificial pericardium of claim 7 wherein each said connector means includes an elastic tube sized to snugly surround its respective line.

17. The artificial pericardium of claim 16 wherein each said connector means includes securing means for placement about said elastic tube to secure said elastic tube to its respective line.

18. The artificial pericardium of claim 7 wherein the closure means is a grooved seal having male and female portions sized for effecting a sealing closure.

19. The artificial pericardium of claim 7 wherein said sac is formed into two sections, wherein said opening is the entire circumference of each section and wherein said closure means is a seal having male and female portions sized for effecting a sealing closure around the entire perimeter of the two sections, said male and female portions being slidable with respect to each other.

20. The artificial pericardium of claim 7 further including an injection site formed in said sac to receive needles therethrough and to seal upon removal thereof for extracting from and injecting fluids into said sac.

21. The artificial pericardium of claim 7 further including internal pressure sensing means positioned within said sac to sense the pressure of fluids therein, said pressure sensing means having means to communicate signals reflective of the sensed pressure via signal communication means to external the body of the patient.

22. The artificial pericardium of claim 7 further including external pressure sensing means positioned exterior the sac on its surface to sense pressure within the body, said external pressure sensing means having means to communicates signals reflective of the sensed pressure via signal communication means to external the body of a patient.

* * * * *